United States Patent
Bae et al.

(10) Patent No.: US 9,724,394 B2
(45) Date of Patent: Aug. 8, 2017

(54) PHARMACEUTICAL COMPOSITION FOR PREVENTING OR TREATING OSTEOPOROSIS WHICH COMPRISES NEUROPEPTIDE Y AS ACTIVE INGREDIENT

(71) Applicant: KYUNGPOOK NATIONAL UNIVERSITY INDUSTRY-ACADEMIC COOPERATION FOUNDATION, Daegu (KR)

(72) Inventors: Jae Sung Bae, Daegu (KR); Hee Kyung Jin, Daegu (KR); Min Hee Park, Gyeongsangbuk-do (KR); Jong Kil Lee, Daegu (KR)

(73) Assignee: KYUNGPOOK NATIONAL UNIVERSITY INDUSTRY—ACADEMIC COOPERATION FOUNDATION, Daegu (KR)

( * ) Notice: Subject to any disclaimer, the term of this patent is extended or adjusted under 35 U.S.C. 154(b) by 0 days.

(21) Appl. No.: 14/773,375

(22) PCT Filed: Feb. 13, 2013

(86) PCT No.: PCT/KR2013/001102
§ 371 (c)(1),
(2) Date: Sep. 7, 2015

(87) PCT Pub. No.: WO2014/106967
PCT Pub. Date: Jul. 10, 2014

(65) Prior Publication Data
US 2016/0243198 A1 Aug. 25, 2016

(30) Foreign Application Priority Data
Jan. 7, 2013 (KR) ........................ 10-2013-0001681

(51) Int. Cl.
*A61K 38/17* (2006.01)
*A61K 38/22* (2006.01)
*A61P 19/10* (2006.01)

(52) U.S. Cl.
CPC ............................. *A61K 38/2271* (2013.01)

(58) Field of Classification Search
None
See application file for complete search history.

(56) References Cited

U.S. PATENT DOCUMENTS

2004/0053864 A1  3/2004  Karsenty et al.
2006/0247156 A1* 11/2006  Vanderby ............. A61K 38/046
                                                514/11.1

FOREIGN PATENT DOCUMENTS

WO   WO-2005/026342 A1   3/2005

OTHER PUBLICATIONS

Lee et al., NPY regulation of bone remodeling, Neuropeptides, 43(6):457-63 (2009). [Abstract only].
Matic et al., Bone-specific overexpression of NPY modulates osteogenesis, J. Musculoskelet. Neuronal Interact., 12(4):209-18 (2012).

* cited by examiner

*Primary Examiner* — Xiaozhen Xie
(74) *Attorney, Agent, or Firm* — Marshall, Gerstein & Borun LLP

(57) ABSTRACT

The present invention relates to a pharmaceutical composition for preventing or treating osteoporosis which comprises neuropeptide Y as an active ingredient. The neuropeptide Y according to the present invention reduces the expression of a cell adhesion factor in osteoblasts in which a Y1 receptor is present, and consequently an effect of releasing a haematopoietic stem cell from bone marrow into the blood is excellent. When a haematopoietic stem cell is released into the blood, the number of osteoclasts which induce an osteoporotic lesion by differentiation from the haematopoietic stem cell decreases, and thus progression of a bone erosion caused by osteoclasts can be prevented. Accordingly, the neuropeptide Y which is an active ingredient of the composition of the present invention is useful as a therapeutic agent for osteoporosis.

12 Claims, 14 Drawing Sheets

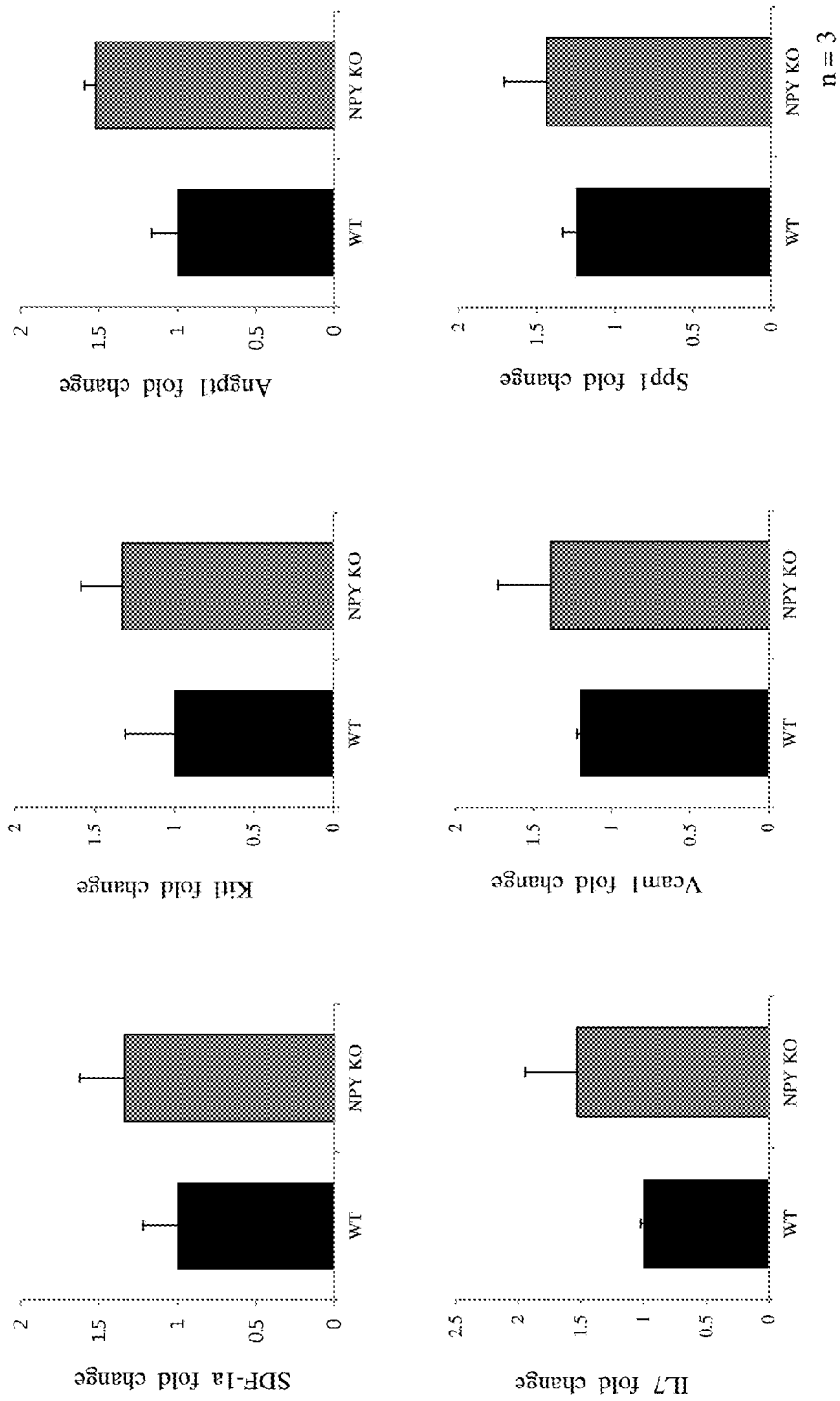
[Fig. 1]

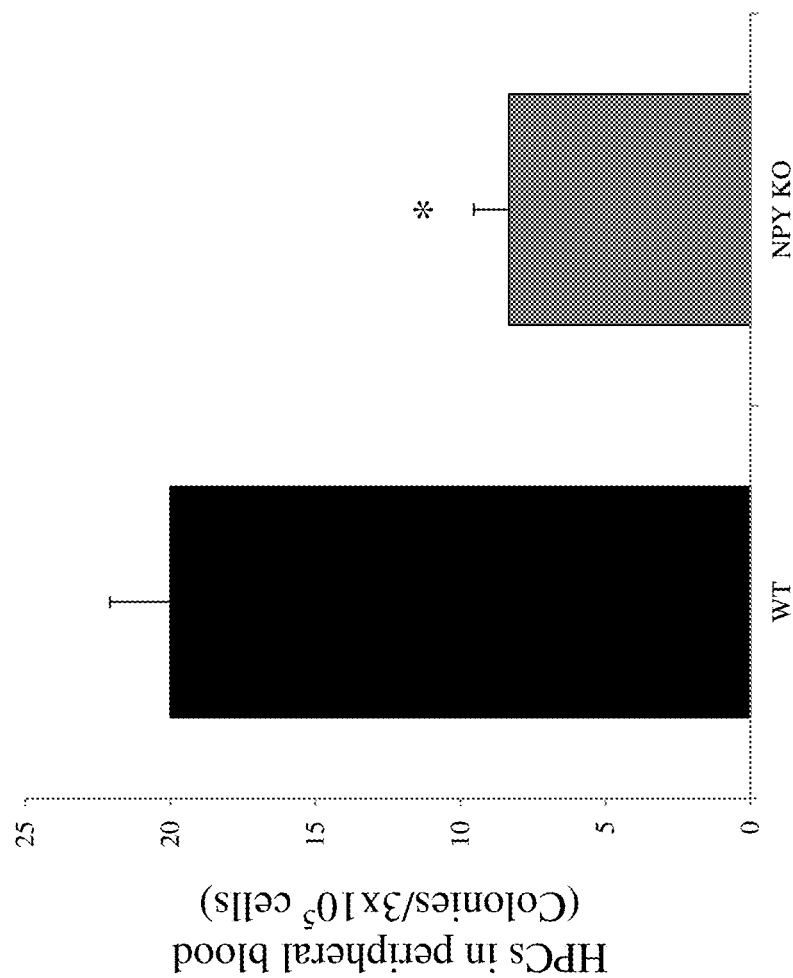
[Fig. 2]

[Fig. 3]
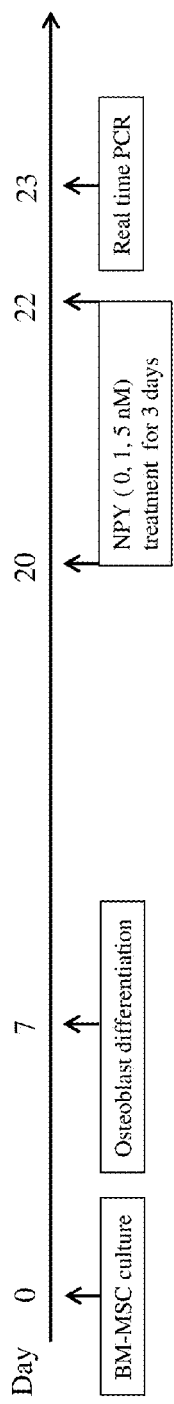
[Fig. 4]
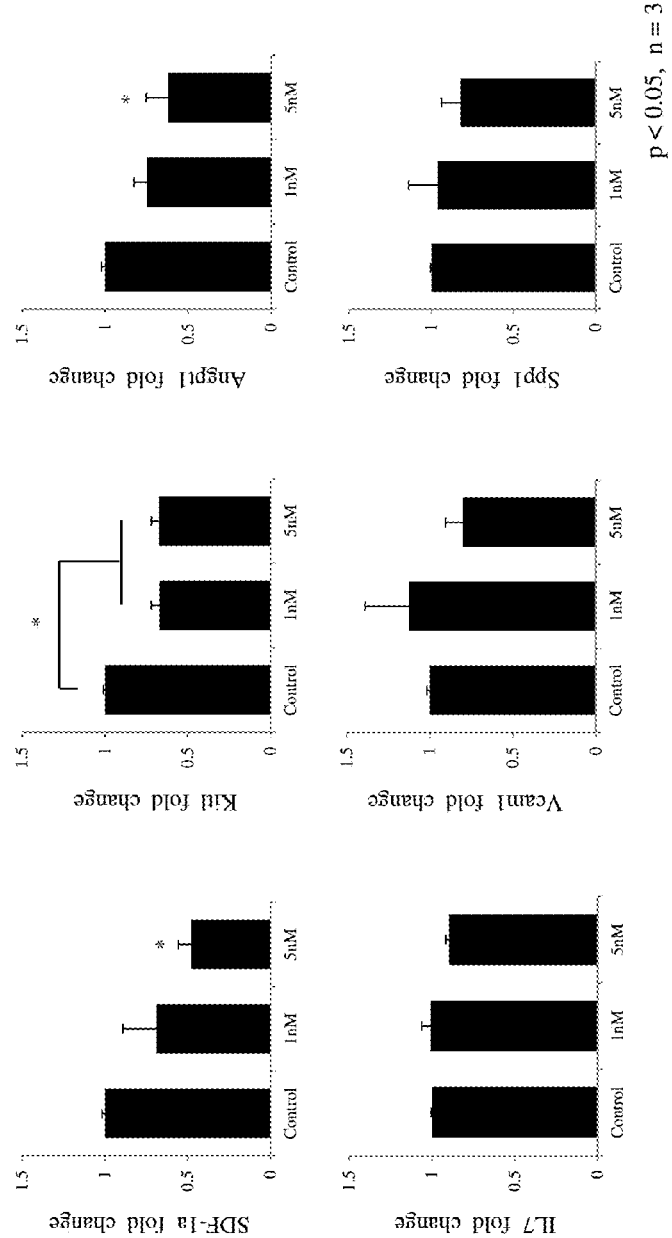

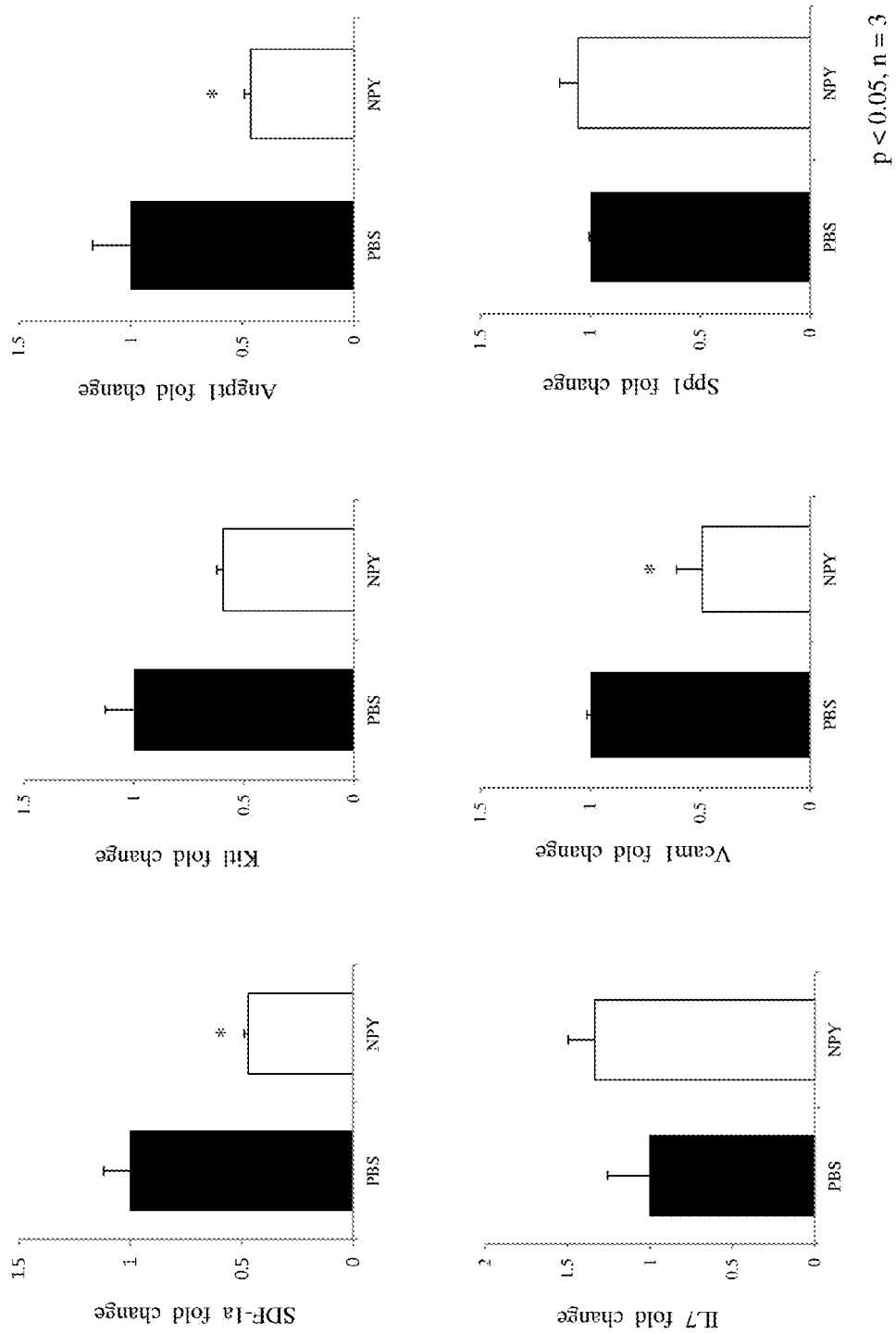

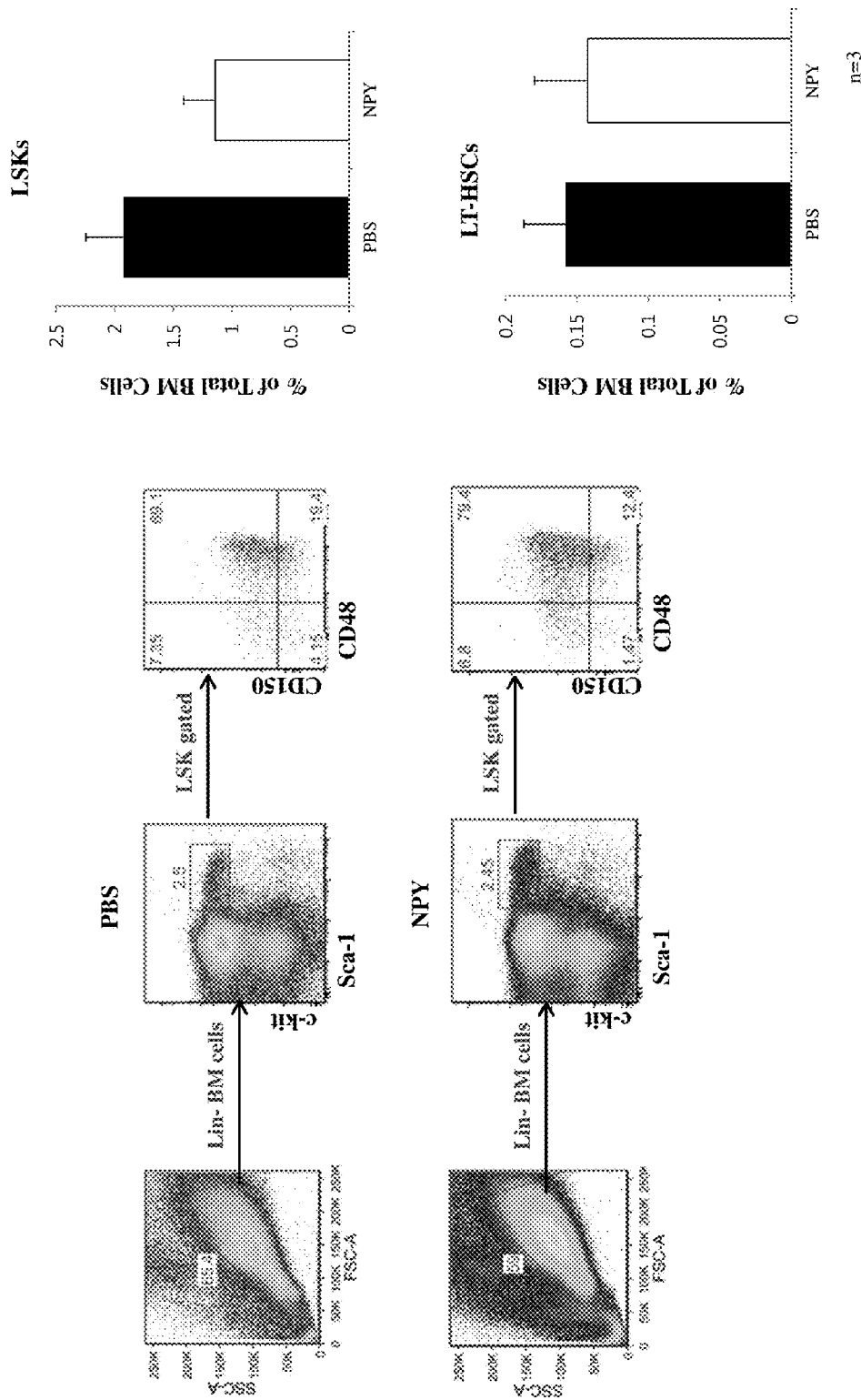
[Fig 7]

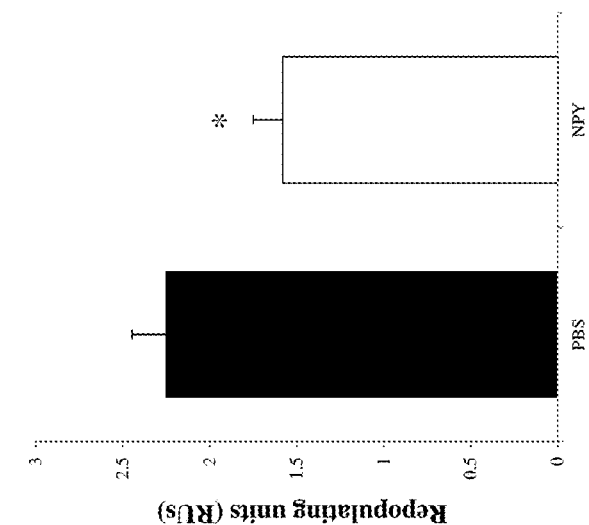
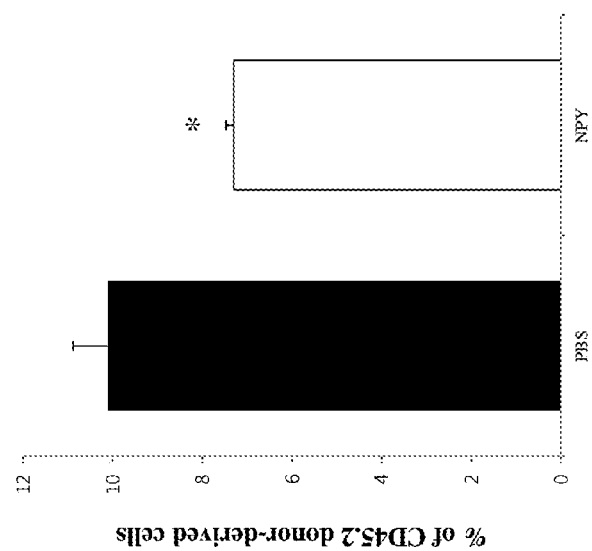
[Fig 8]

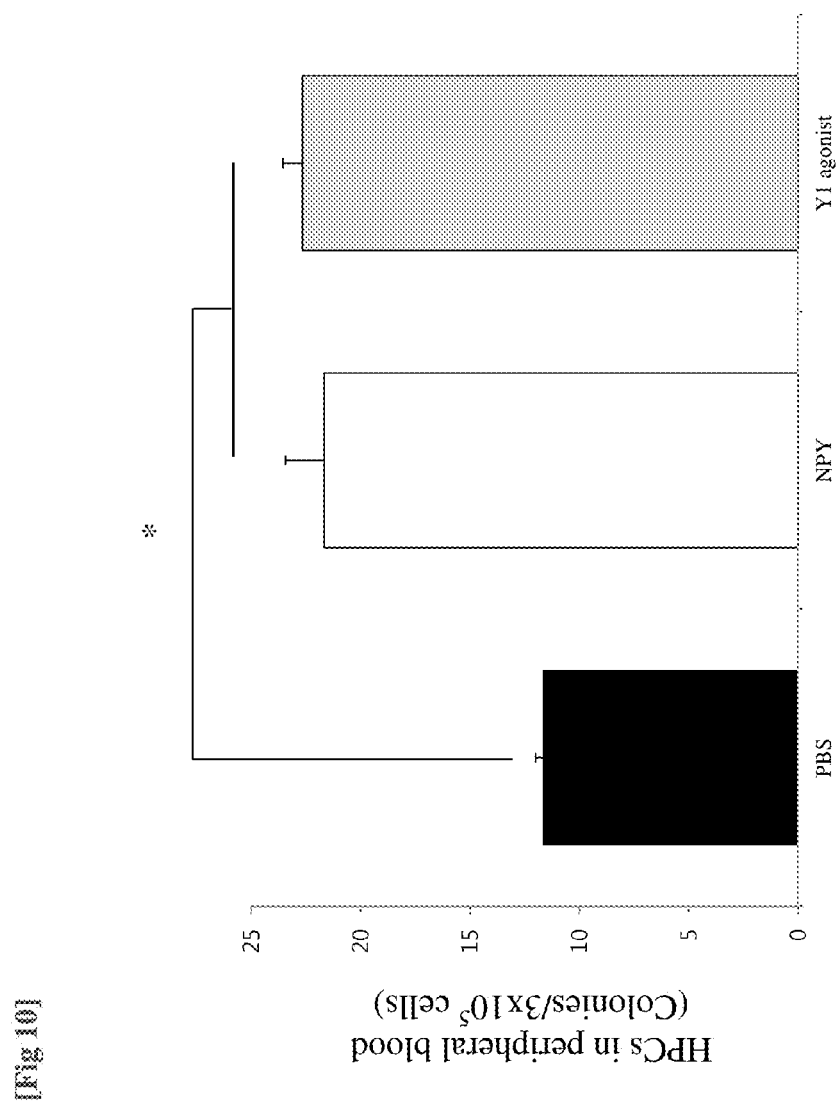
[Fig. 10]

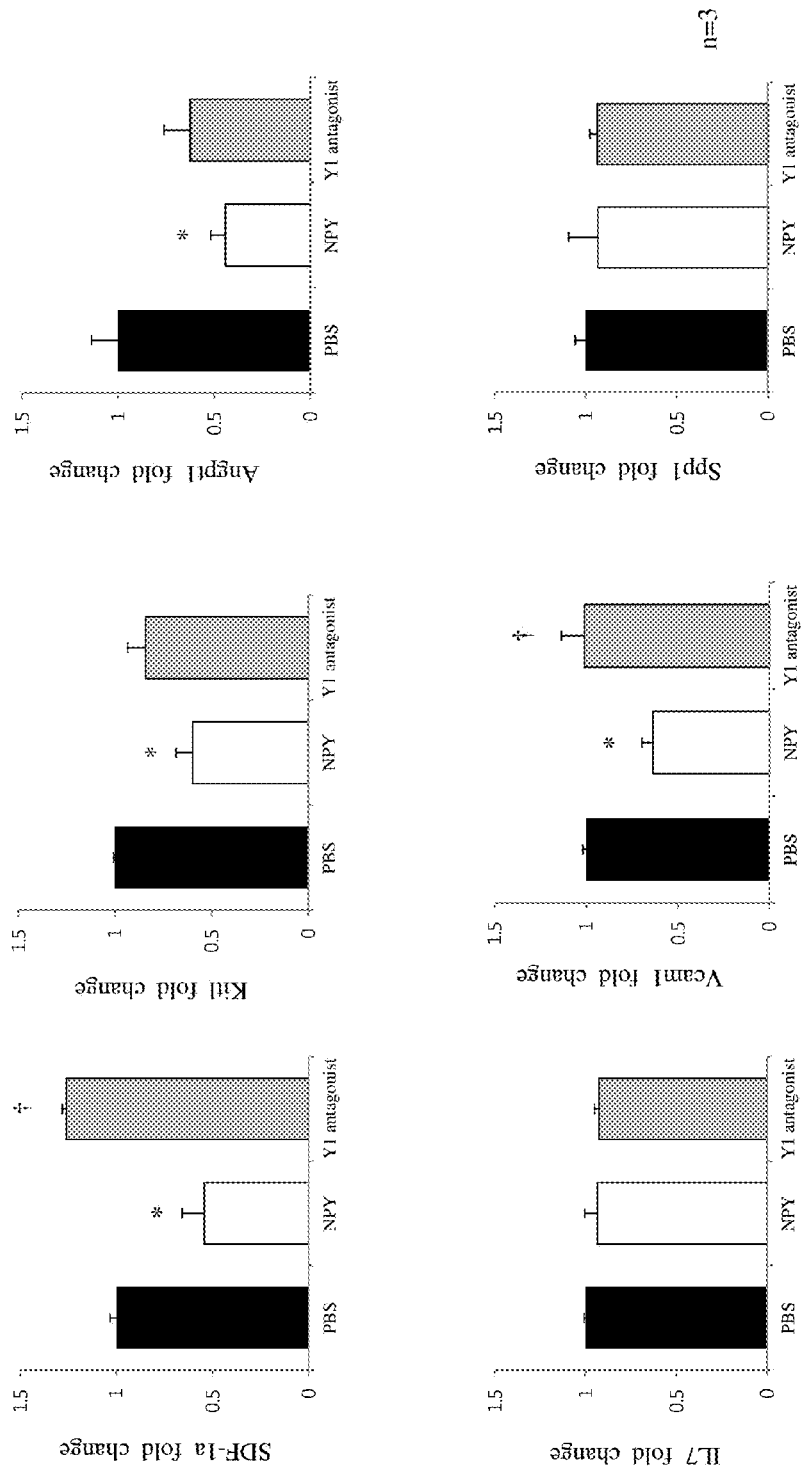
[Fig. 11]
* p<0.05 vs PBS i.v mice, † p<0.05 vs NPY i.v mice

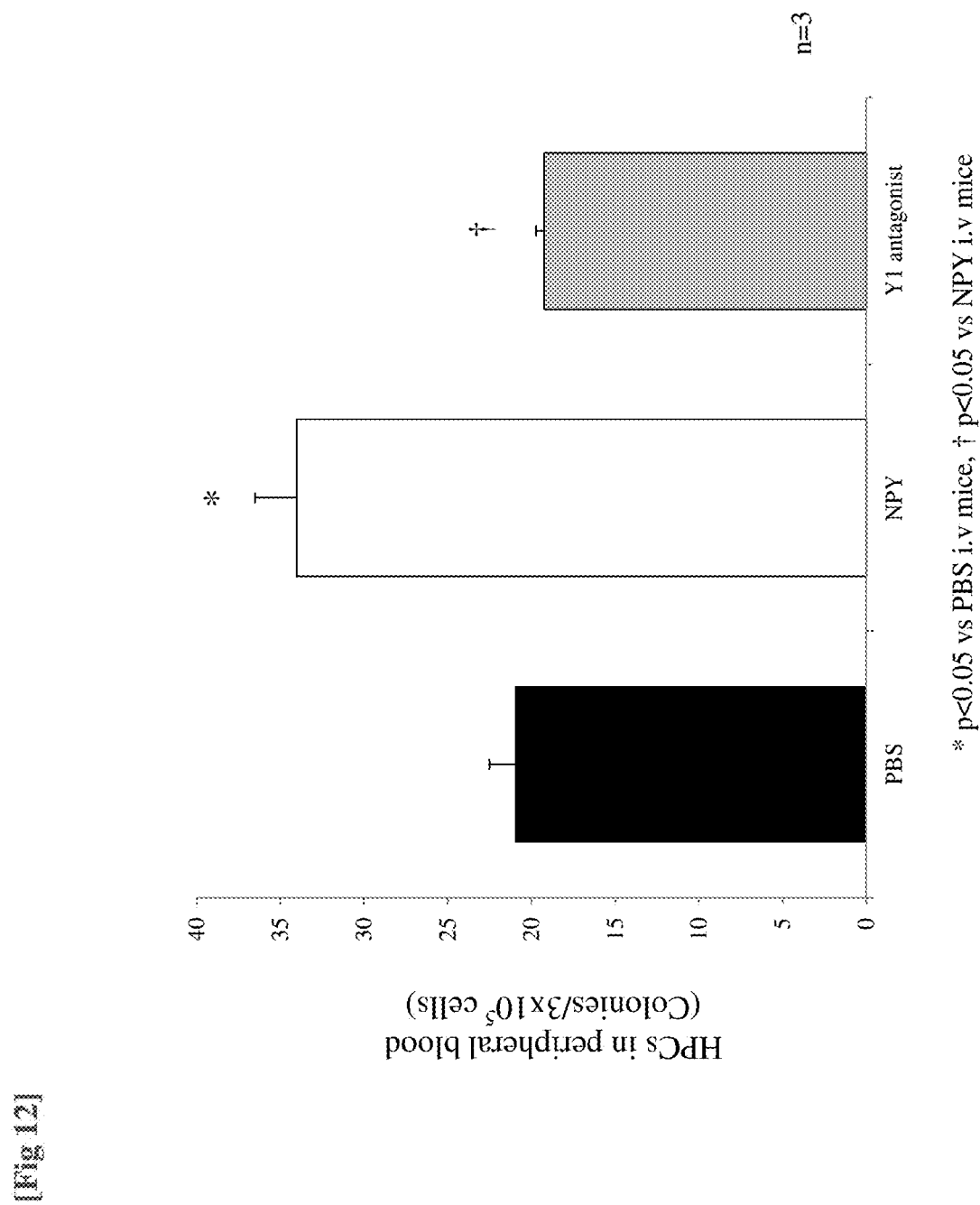
[Fig. 12]

[Fig 13]
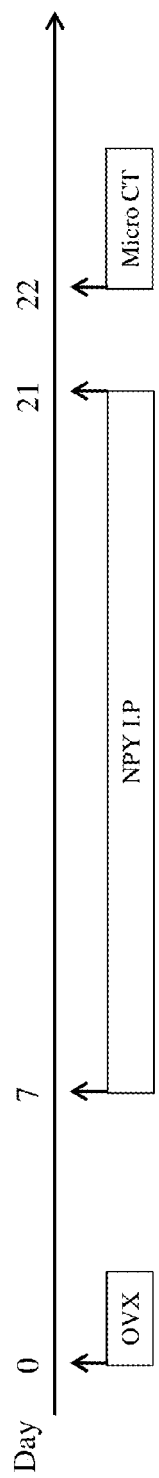
[Fig 14]
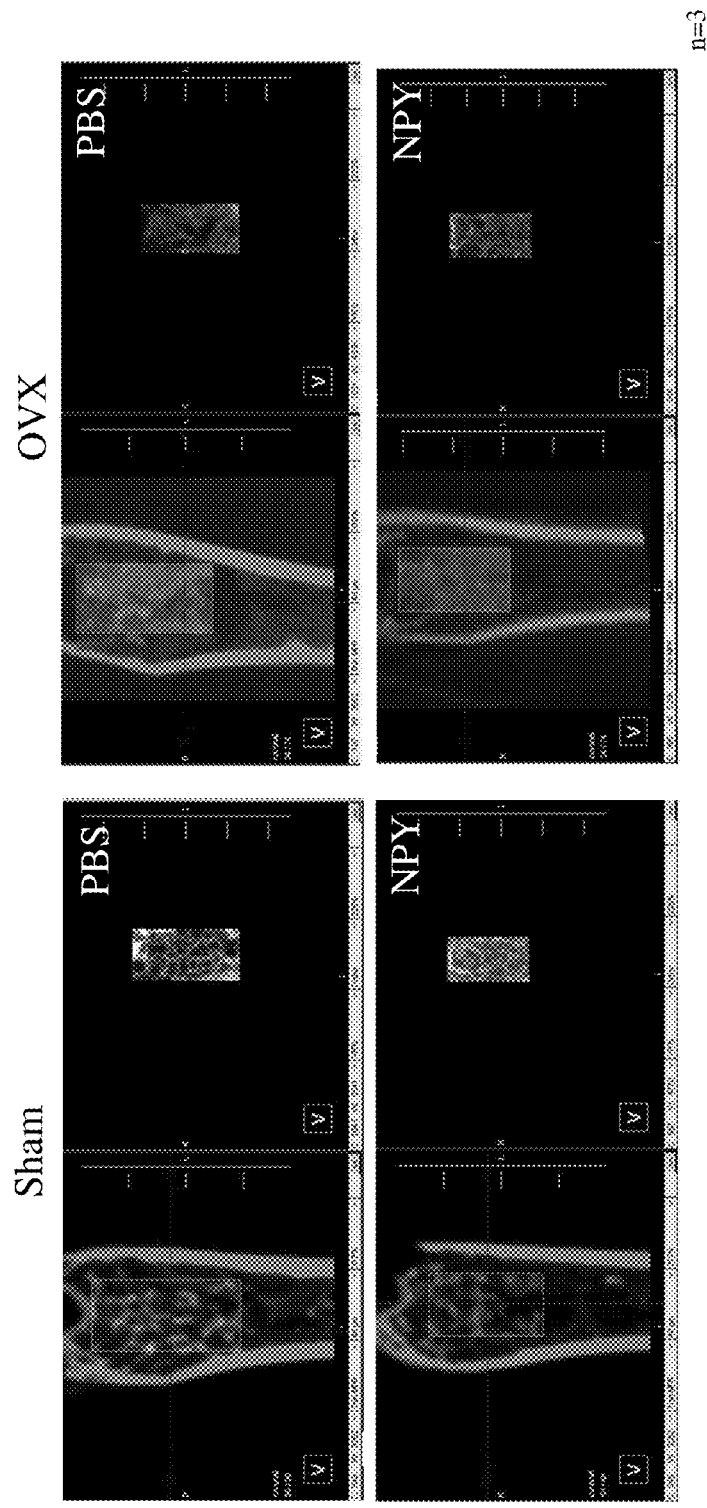

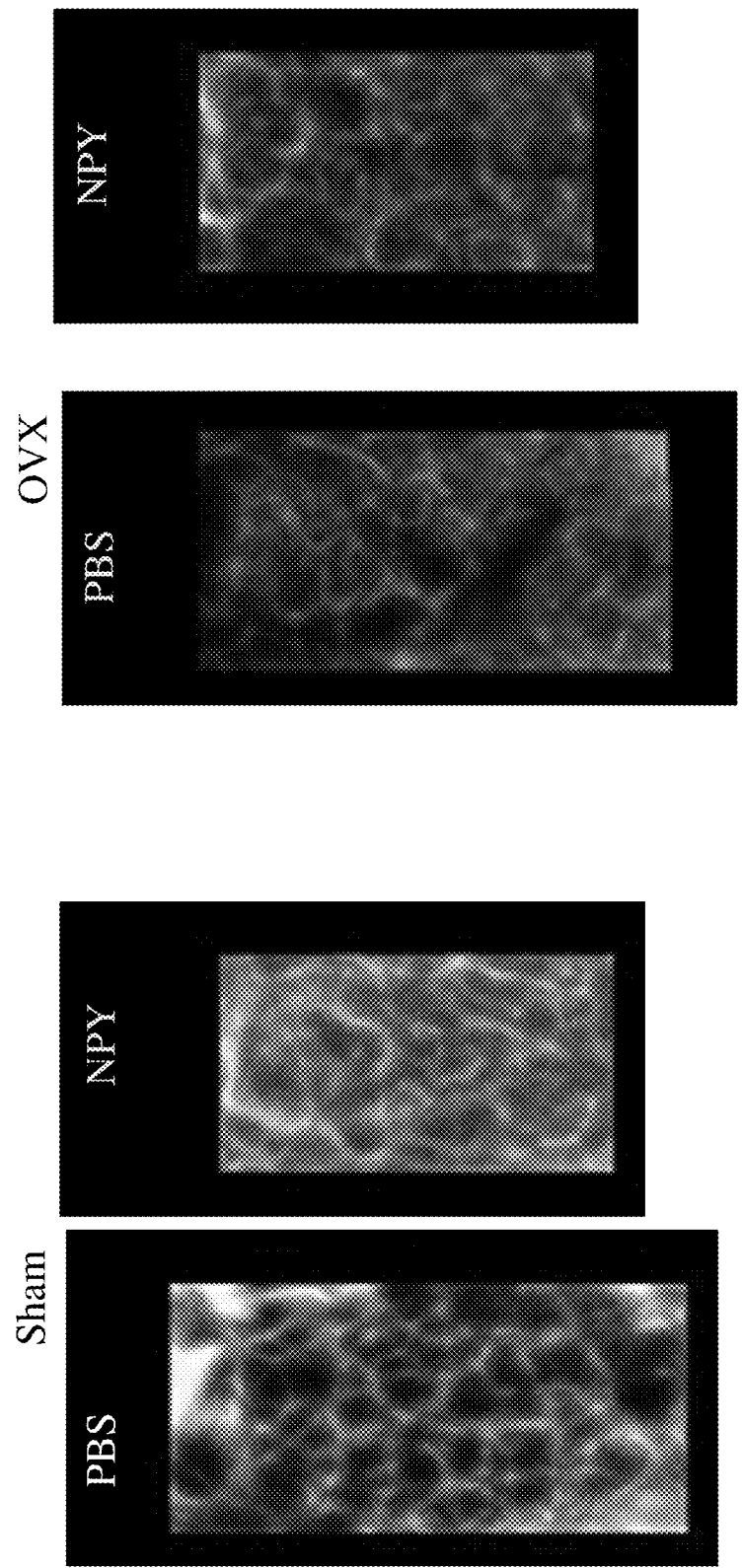
[Fig 14a]

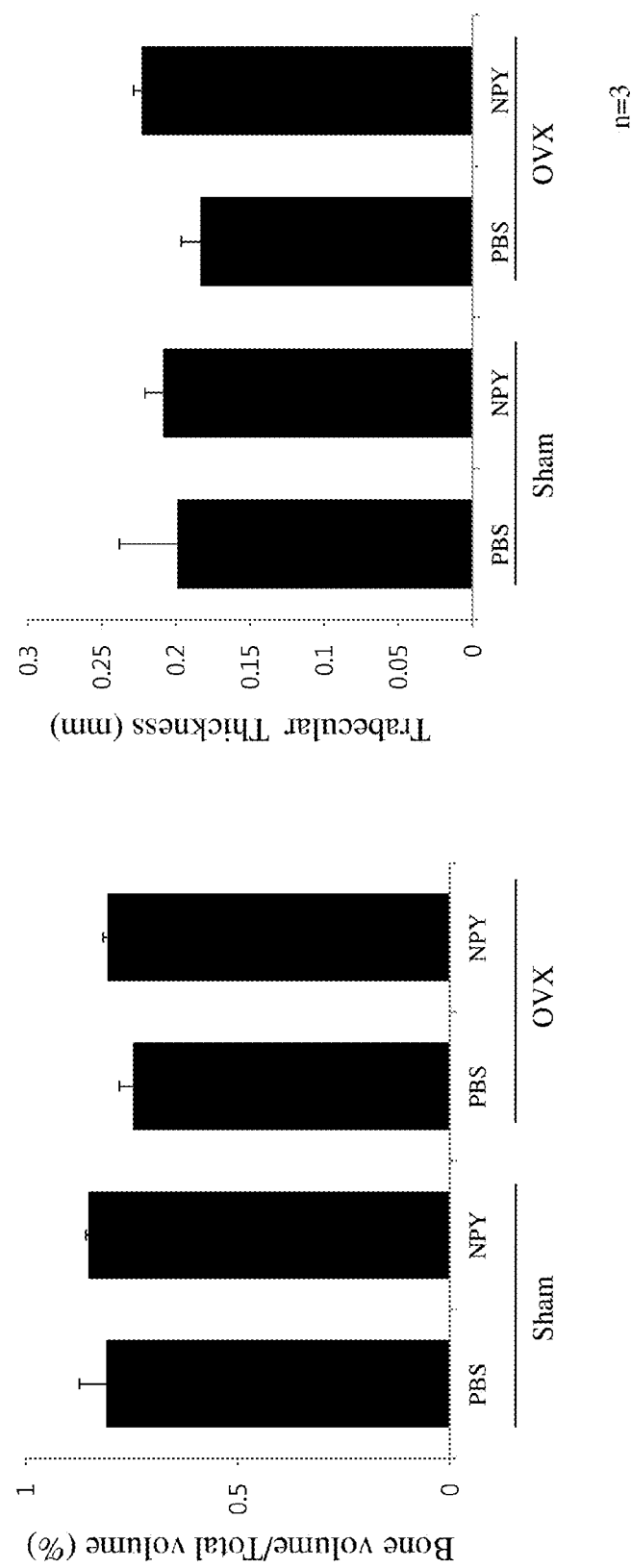
[Fig 15]

SEQUENCE LISTING

<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: Synthetic primer

<400> SEQUENCE: 1
ttcctatcag agcccataga g                    21

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
ccagaccatc ctggataatg                      20

<210> SEQ ID NO 3
<211> LENGTH: 23

```
<212> TYPE: DNA
<213> ORGANISM: Artificial Sequence
<220> FEATURE:
<223> OTHER INFORMATION: Synthetic primer

<400> SEQUENCE: 3
ccaaaagcaa agccaattac aag                                        23

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
agactcgggc ctacaatgga                                            20

<210> SEQ ID NO 5
<211> LENGTH: 18
<212> TYPE: DNA
<213> ORGANISM: Artificial Sequence
<220> FEATURE:
<223> OTHER INFORMATION: Synthetic primer

<400> SEQUENCE: 5 acggggtca attctaag                                               18

<210> SEQ ID NO 6
<211> LENGTH: 18
<212> TYPE: DNA
<213> ORGANISM: Artificial Sequence
<220> FEATURE:
<223> OTHER INFORMATION: Synthetic primer

<400> SEQUENCE: 6
gccattcctg actccaca                                              18

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
aaaagcggag acaggagaca                                            20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
agcacgagaa gctcaggaga                                            20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
```

```
attgaacctg cagaccaagc                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
gcaacagaac aaggatcagg                                              20

<210> SEQ ID NO 11
<211> LENGTH: 30
<212> TYPE: DNA
<213> ORGANISM: Artificial Sequence
<220> FEATURE:
<223> OTHER INFORMATION: Synthetic primer

<400> SEQUENCE: 11
tgtggagttt tagagatatt agatagtggg                                   30

<210> SEQ ID NO 12
<211> LENGTH: 28
<212> TYPE: DNA
<213> ORGANISM: Artificial Sequence
<220> FEATURE:
<223> OTHER INFORMATION: Synthetic primer

<400> SEQUENCE: 12
aacacactct taacaccact aaatcacc                                     28

<210> SEQ ID NO 13
<211> LENGTH: 21
<212> TYPE: DNA
<213> ORGANISM: Artificial Sequence
<220> FEATURE:
<223> OTHER INFORMATION: Synthetic primer

<400> SEQUENCE: 13
ttgctgttga agtcgcagga g                                            21

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
tgtgtccgtc gtggatctga                                              20
```

PHARMACEUTICAL COMPOSITION FOR PREVENTING OR TREATING OSTEOPOROSIS WHICH COMPRISES NEUROPEPTIDE Y AS ACTIVE INGREDIENT

TECHNICAL FIELD

The present invention relates to a pharmaceutical composition for preventing or treating osteoporosis which include neuropeptide Y as an active ingredient.

BACKGROUND ART

Osteoporosis can be classified into postmenopausal osteoporosis, which occurs with an increase in bone resorption caused by activation of osteoclasts due to sudden changes in hormones after menopause, and senile osteoporosis, in which osteogenesis declines due to a decrease in functions of the osteoblasts in elderly men and women. Bone fractures caused by such osteoporosis severely restricts patients' activities. Since hip fractures are associated with a high mortality of approximately 15 to 35%, it is important to diagnose and treat osteoporosis before the onset of osteoporotic bone fractures.

In 2008, it was reported that the prevalence rate of osteoporosis in Korea has increased by approximately 3 times over the last 5 years, and the yearly socioeconomic loss caused by the osteoporosis bone fractures reaches a serious level of approximately 1.05 trillion won. Also, in 2009, the latest Korea Health Statistics show that the prevalence rates of osteoporosis in the total Korean populations over 50 years old and 65 years old are 23.1% and 42.0%, respectively. Among chronic diseases, osteoporosis has immerged as a big issue in national health due to a very high prevalence rate (Korean National Health and Nutrition Examination Survey in 2009).

Therapeutic agents for osteoporosis known in the prior art are bisphosphonate-based drugs. Bisphosphonate is known to deposit into inorganic components of bone, show toxicity to cells with formation of ATP analogues, which are not hydrolyzed when the bone into which bisphosphonate deposits is phagocytized by osteoclasts, or reduce the osteoclast activities in osteoclasts in various manners and cause apoptosis to reduce the bone resorption, thereby causing an increase in bone density. Although such drugs are known to be relatively safe, the drugs have problems in that they may affect the remodeling of bone by normal bone resorption and formation, or bone healing after bone fracture when they are used for a long period of time, and thus cause a decrease in bone elasticity, resulting in an adverse effect on bone strength. In fact, it was reported that stress fractures occur due to the decrease in bone elasticity in many patients.

Therefore, there is an urgent need for finding of a novel bone mechanism associated with the onset of osteoporosis, and prevention of osteoporosis or development of therapeutic agents.

Typically, the bone remodeling (i.e., bone regeneration) has been considered to be mainly regulated by the endocrine system, and locally acting factors such as cytokines, growth factors, etc. However, such a point of view has gradually changed with the evidence that neurological factors can alter the activities of osteocytes. In recent years, much research shows that nerve fibers and neurological factors are found in bone tissues, which supports these facts.

As a sympathetic neurotransmitter, neuropeptide Y (NPY) is a neurotransmitter which is found most abundantly in the brains of mammals, and consists of 36 amino acids. Such a neurotransmitter is known to secrete from a Y2 receptor in the hypothalamus, and play parts in various physiological and pathological conditions such as the control of appetite, memories, and seizure (Balasubramaniam, 1997; Vezzani et al., 1999; Wettstein et al., 1995). In this regard, it was reported that, when our bodies are exposed to stress environments, the secretion of neuropeptide Y from the brain and sympathetic nervous system increases, resulting in obesity due to an increase in phagocytosis. However, there are no research reports known an effect of neuropeptide Y on functional control, release, and homing of bone marrow-derived stem cells such as haematopoietic stem cells, differentiated cells, and immune-related cells, etc. In particular, the relationship between neuropeptide Y andosteoporosis remains to be found.

The present inventors have found that neuropeptide Y may be used to induce the release of haematopoietic stem cells from the bone marrow into blood so as to prevent or treat osteoporosis. Therefore, the present invention has been completed based on these facts.

DISCLOSURE

Technical Problem

Therefore, it is an aspect of the present invention to provide a pharmaceutical composition for preventing or treating osteoporosis, which includes neuropeptide Y as an active ingredient.

Technical Solution

According to an aspect of the present invention, there is provided a pharmaceutical composition for preventing or treating osteoporosis, which includes neuropeptide Y as an active ingredient.

Advantageous Effects

The neuropeptide Y according to one exemplary embodiment of the present invention can reduce the expression of a cell adhesion factor in osteoblasts in which a Y1 receptor is present, and thus show an excellent effect of releasing haematopoietic stem cells from the bone marrow into blood. When the haematopoietic stem cells are released into the blood, the number of osteoclasts which differentiates from the haematopoietic stem cells to induce an osteoporotic lesion decreases, thereby preventing the progression of bone erosion caused by the osteoclasts. Accordingly, the neuropeptide Y which is an active ingredient of the composition of the present invention is useful as a therapeutic agent for osteoporosis.

DESCRIPTION OF DRAWINGS

FIG. 1 is a diagram showing expression levels of bone-marrow haematopoietic stem cell adhesion factor in neuropeptide Y-knockout (NPY KO) mice and wild-type (WT) mice.

FIG. 2 is a diagram showing the number of bone-marrow hematopoietic progenitor cells in blood in the NPY KO mice and WT mice.

FIG. 3 is a diagram showing an experimental overview of the present invention, which is performed to determine an effect of neuropeptide Y according to one exemplary embodiment of the present invention on the expression level of the bone-marrow haematopoietic stem cell adhesion factor.

FIG. 4 is a diagram showing the results obtained for an effect of neuropeptide Y according to one exemplary embodiment of the present invention on the expression level of the bone-marrow haematopoietic stem cell adhesion factor according to the concentration of neuropeptide Y.

FIG. 5 is a diagram showing a change in the expression level of the bone-marrow haematopoietic stem cell adhesion factor when the neuropeptide Y according to one exemplary embodiment of the present invention is administered.

FIG. 7 is a diagram showing a level of release of the bone-marrow haematopoietic stem cells into blood using a marker for bone-marrow haematopoietic stem cells upon administration of the neuropeptide Y according to one exemplary embodiment of the present invention.

FIG. 8 is a diagram showing, as the results of competitive transplantation experiments, a level of release of the bone-marrow haematopoietic stem cells into blood upon administration of the neuropeptide Y according to one exemplary embodiment of the present invention.

FIG. 10 is a diagram showing the number of the bone-marrow hematopoietic progenitor cells in blood upon administration of the neuropeptide Y receptor agonist.

FIG. 11 is a diagram showing a change in the expression level of the bone-marrow haematopoietic stem cell adhesion factor upon administration of a neuropeptide Y receptor antagonist (a Y1 antagonist).

FIG. 12 is a diagram showing the number of the bone-marrow hematopoietic progenitor cells in blood upon administration of the neuropeptide Y receptor antagonist.

FIG. 13 is a diagram showing an experimental overview performed to determine an effect of neuropeptide Y according to one exemplary embodiment of the present invention on prevention and treatment of osteoporosis.

FIG. 14 is a diagram obtained by photographing bones with micro-CT, and imaging an entire change in bone density upon administration of neuropeptide Y in an osteoporosis model.

FIG. 14a provides enlarged views of the micro-CT photograph images from FIG. 14.

FIG. 15 is a diagram obtained by photographing a change in bone density and a change in trabecular thickness upon administration of neuropeptide Y with micro-CT, and quantifying the changes in bone density and trabecular thickness as a graph in the osteoporosis model.

BEST MODE

Figure 6:
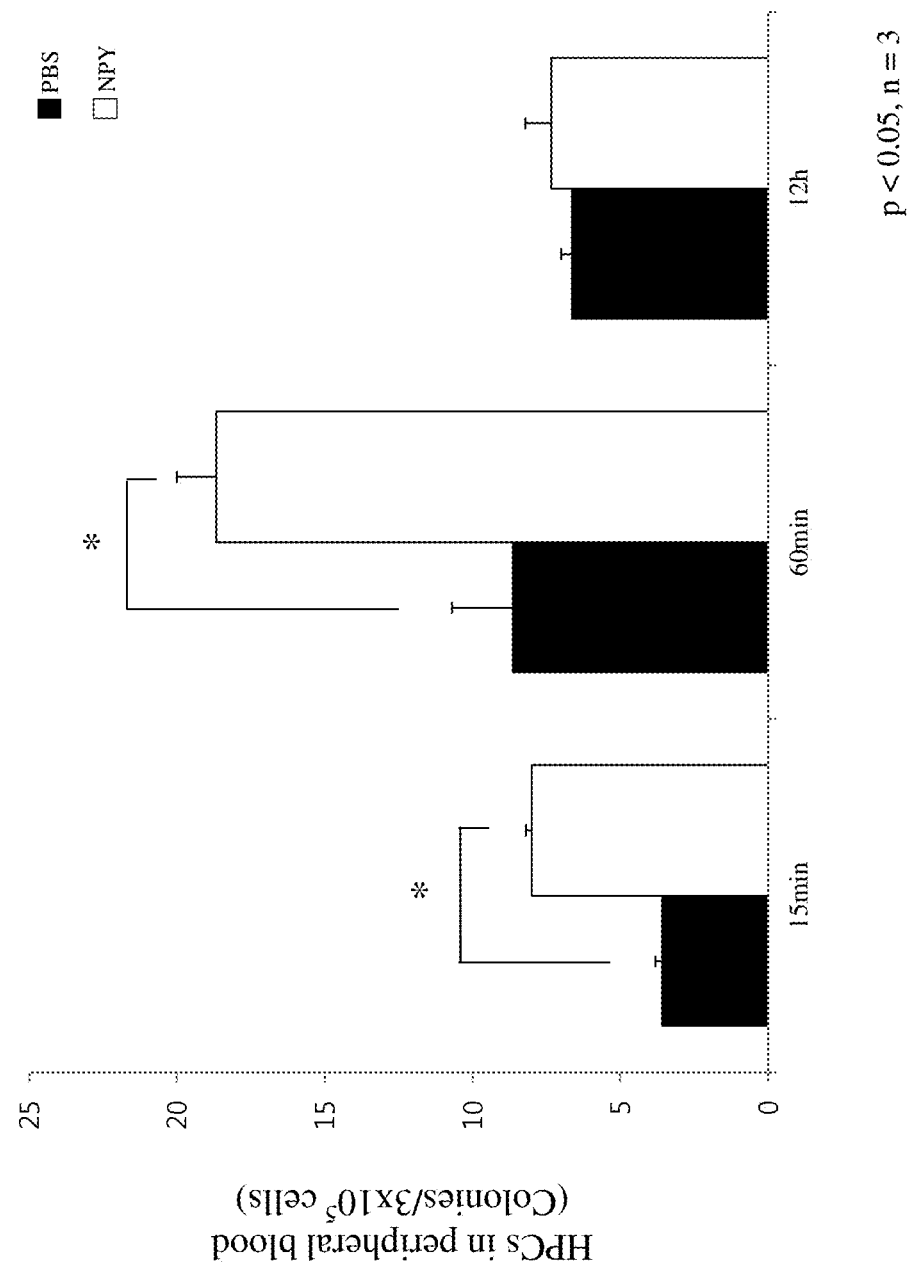
FIG. 6 is a diagram showing the number of the bone-marrow hematopoietic progenitor cells in blood according to the lapse of time upon administration of the neuropeptide Y according to one exemplary embodiment of the present invention.

The present invention provides a pharmaceutical composition for treating osteoporosis, which includes neuropeptide Y as an active ingredient.

Hereinafter, the present invention will be described in detail.

The term "stem cell niche" refers to a microenvironment which is found in stem cells, and in which the stem cells interact to control the fate of the stem cells. The term "niche" may refer to an in vivo and in vitro microenvironment of stem cells. In the embryo development phase, various niche factors act on embryonic stem cells to have an influence on the expression of genes, and induce cell growth or differentiation to develop a fetus. However, adult stem cells are maintained in a resting state in adults, but, when tissues or cells are damaged, microenvironments of tissues neighboring the damaged tissues or cells actively send signals to niches in which stem cells are present so as to promote differentiation of stem cells present in the niches for the purpose of self-renewal of the stem cells or formation of new tissues.

The interaction between stem cells and neighboring differentiated cells or adhesion molecules, extracellular matrix elements, growth factors, cytokines, physiochemical environments such as pH, the ionic strength such as calcium ion concentration, metabolites such as ATP, and the cell-cell interaction between the stem cells are known to be important in regulating the characteristics of the stem cells in the stem cell niche. Also, it is known that reversible signals for maintaining the stem cells may be sent and received between the stem cells and the stem cell niches in both of a developmental stage and an adult stage.

The hippocampus in the brain, neural stem cell niches of the lateral ventricle, bone-marrow stem cell niches in the bone marrow, and the like are known to be present in a human body. Among theses, the bone-marrow stem cell niches are defined as molecular microenvironments in which the functions and fates of the cells are controlled by means of interaction between various cells preset in the bone marrow, including the bone marrow stem cells. Generally, two bone-marrow stem cell niches, for example, an "endosteal niche" and a "perivascular niche," are known so far.

First, the "endosteal niche" is a microenvironment in which basal cells are present in the bone marrow, and is present mainly in the basal cells, osteoblasts, osteoclasts, etc. Here, the endosteal niche is a bone-marrow stem cell niche in which these cells are adjacent to other cell, especially hematopoietic progenitor cells (HPCs) or haematopoietic stem cells (HSCs) by means of adhesion factors (CXCL12, Ang-1, VCAM1, stem cell factor, IL-7, etc.), and react with neurotransmission signals introduced from the outside to release haematopoietic stem cells attached to osteoblasts into blood, or home the bone marrow so as to have an influence on maintenance of homeostasis in the bone marrow.

Also, the "perivascular niche" refers to a microenvironment which is composed of macrophages, bone-marrow mesenchymal stem cells (MSCs), and CXCL12 abundant reticular (CAR) cells. Here, the perivascular niche is a bone-marrow stem cell niche in which these cells are adjacent to haematopoietic stem cells by means of intercellular adhesion factors like the endosteal niche, and are involved in reacting with neurotransmission signals introduced from the outside, such as stress, neurotransmitters, etc., to release macrophages, haematopoietic stem cells harboring the mesenchymal stem cells, etc. into blood.

As described above, the release (i.e., mobilization) of stem cells in the bone marrow into the bloodstream or the homing of the released stem cells in the bone marrow occurs in the bone marrow niche. The release (i.e., mobilization) of the stem cells in the bone marrow into the blood is an important process which occurs in the bone marrow when our bodies are under stress or damaged, in a process of which the stem cells, immune-related cells, and osteoclasts mobilize from the bone marrow into blood vessels. Here, the cells mobilized into the blood vessels flow through the bloodstream to a lesion site in which the cells are damaged, and help to heal the lesion site. Meanwhile, the stem cells in the bone marrow in which the healing process in such a lesion site is completed return to the bone marrow through the bloodstream, a process of which is referred to as "homing."

The neuropeptide Y which is the active ingredient of the present invention may be obtained by in vivo extraction using a conventional method, or a commercially available neuropeptide Y may be purchased and used herein.

When the neuropeptide Y which is the active ingredient of the present invention is administered in vivo, the neuropeptide Y has an effect of reducing the expression of adhesion factors involved in maintenance of the bone-marrow haematopoietic stem cells in the bone marrow, and thus shows an excellent effect of inducing the release of the bone-marrow haematopoietic stem cells or bone-marrow hematopoietic progenitor cells, either of which are maintained in the bone marrow, into blood.

The bone-marrow haematopoietic stem cells may differentiate into lymphocytic cells and myeloid cells in the bone marrow. As a kind of the myeloid cells differentiated from the bone-marrow haematopoietic stem cells, osteoclasts serve to maintain bone formation and erosion actions by means of the balance with the osteoblasts in the bone marrow. When such a balance collapses, an increase in the number of osteoclasts, and an increase in rate of bone erosion are accelerated to cause the onset of osteoporosis.

It was known that, when a substance for inducing the release of precursor cells of the osteoclasts into blood, sphingosine-1-phosphate (S1P), is administered, or an agonist (FTY720) against a S1P receptor is administered so as to reduce the number of the osteoclasts in the bone marrow, the bone formation increases (Nature, 2009; Masaru Ishii et al.). Similarly, when the release of the bone-marrow haematopoietic stem cells, which are primordial cells of the osteoclasts, into the blood is induced, the number of the osteoclasts in the bone marrow decreases with a decrease in the differentiation into osteoclasts.

As described above, the decrease in the number of the osteoclasts caused by the release of the haematopoietic stem cells into the blood suppresses the progression of an osteoporotic lesion by reducing the bone erosion by the osteoclasts. Therefore, the neuropeptide Y according to one exemplary embodiment of the present invention may be effectively to prevent or treat osteoporosis by inducing the release of the haematopoietic stem cells into blood to reduce the differentiation into osteoclasts in the bone marrow.

The composition according to one exemplary embodiment of the present invention may include at least one active ingredient, which is effective in preventing or treating osteoporosis, in addition to the neuropeptide Y.

The composition according to one exemplary embodiment of the present invention may be prepared to further include at least one pharmaceutically available carrier in addition to the active ingredient as described above for the purpose of administration. The pharmaceutically available carrier may be used in combination with at least one selected from the group consisting of saline, sterile water, a Ringer's solution, buffered saline, a dextrose solution, a maltodextrin solution, glycerol, ethanol and a mixture thereof. As necessary, another typical additive such as an antioxidant, a buffer, and a bacteriostatic agent may be added. Also, a diluent, a dispersing agent, a surfactant, a binder, and a lubricant are further added to the composition, which may then be formulated into an injectable formulation such as an aqueous solution, a suspension, or an emulsion, a pill, a capsule, a granule, or a tablet. Further, the composition may be desirably formulated according to diseases or ingredients using a proper method known in the related art, or a method disclosed in Remington's Pharmaceutical Science (the latest version), Mack Publishing Company, Easton Pa.

The composition according to one exemplary embodiment of the present invention may be administered orally, or administered parenterally (for example, intravenous, subcutaneous or intraperitoneal, or local application) according to a desired method. The dose of the composition may vary according to the body weight, age, sex, and health condition of a patient, diet, an administration time, a method of administration, a release rate, and severity of a disease. The daily dose of the neuropeptide Y is in a range of approximately 0.01 to 1 mg/kg, preferably approximately 0.05 to 0.1 mg/kg. In this case, the neuropeptide Y is preferably administered once a day, or administered in divided doses.

The composition according to one exemplary embodiment of the present invention may be used alone to prevent or treat osteoporosis or increase the bone density, or may be used in combination with surgery, hormone therapy, drug treatment, and methods using a biological response modifier.

MODE FOR INVENTION

Hereinafter, preferred Examples are provided to aid in understanding the present invention. However, it should be understood that detailed description provided herein is merely intended to provide a better understanding of the present invention, and is not intended to limit the scope of the present invention.

Example 1. Materials and Methods for Experiments 1-1. Preparation of Mice and Drug Treatment Protocol All mice used in this experiment were 6 weeks old to 8 weeks old, and divided into NPY KO mice in which a neuropeptide Y (NPY) gene was genetically knock out, NPY wild-type (WT) mice, Ly5.1 (BoyJ) mice, and Ly5.2 (C57BL/6) mice, all of which were purchased from Jackson Laboratory (Bar Harbor, Me., USA), and used.

Neuropeptide Y, a Y1 agonist, and a Y1 antagonist were purchased from Bache, and used. To perform an in vitro experiment, 1 nM NPY, and 5 nM NPY were diluted with a medium, and injected. For the in vivo experiment, a total of 15 mice (three mice in each group) were also anesthetized with a mixed solution of 100 mg/kg ketamine and 10 mg/kg xylazine, and 50 μg/kg of either neuropeptide Y, Y1 agonist, or Y1 antagonist, and 100 μl of PBS (Gibco) were injected through the tail veins of the mice.

Also, a total 6 female mice (three mice in each group), 12 weeks old, were subjected to an ovariotomy to establish an osteoporosis model. After a week, 50 μg/kg of neuropeptide Y and 100 μl of PBS (Gibco) were abdominally administered twice a day to the female mice at an interval of 12 hours for 3 weeks. As the control, a total 6 female mice (three mice in each group) were subjected to an ovariotomy to establish a Sham model for osteoporosis. In this case, 100 μl of PBS or 50 μg/kg of neuropeptide Y was abdominally administered.

1-2. Culture of Bone-Marrow Mesenchymal Stem Cells and Induction of Differentiation into Osteoblasts Four- to six-week-old C57BL/6 mice were anesthetized, and sacrificed, and their tibias and femurs were incised. The bone marrows were collected from the tibias and femurs, and a single-cell suspension was obtained using a 40-μm cell strainer (Becton-Dickinson LAβware, Franklin Lakes, N.J.). Approximately $10^7$ cells were divided into a 75-cm² flask containing mesenchymal stem cell stimulatory supplements supplemented with an antibiotic, and a MesenCult™ MSC basal medium. The cells were cultured for 1 week, and then cultured in a StemXVivo Osteogenic/Adipogenic Base medium (R&D Systems) supplemented with a StemXVivo Osteogenic supplement (20×) and penicillin-streptomycin (100×) for 3 weeks to differentiate into osteoblasts. In this case, the culture medium was replaced at intervals of 2 to 3 days.

1-3. Real-Time Quantitative PCR

To measure expression levels of haematopoietic stem cell adhesion factors (Sdf-1a, Kit1, Angpt1, IL7, Vcam1, and Spp1) present in the osteoblasts, a real-time quantitative polymerase chain reaction (PCR) method was used.

A total of RNAs were extracted from a cell lysate and bone marrow cells using an RNeasy Plus Mini kit (Qiagen, Korea, Ltd), and cDNA was synthesized from a total of 5 μg of RNA using a kit commercially available from Clontech (Mountain View, Calif.). Also, real-time quantitative PCR, which included denaturation at 95° C. for 10 minutes; and 40 cycles with one cycle consisting of denaturation at 95° C. for 10 seconds, annealing at 58° C. for 15 seconds, and extension at 72° C. for 20 seconds, was performed using a Corbett research RG-6000 real-time PCR machine.

Primers used in the real-time quantitative PCR are listed in the following Table 1.

TABLE 1

| | | | SEQ ID NO: |
|---|---|---|---|
| SDF-1 α | F | 5'-TTCCTATCAGAGCCCATAGAG-3' | 1 |
| | R | 5'-CCAGACCATCCTGGATAATG-3' | 2 |
| Kit ligand (stem cell factor; SCF) | F | 5'-CCAAAAGCAAAGCCAATTACAAG-3' | 3 |
| | R | 5'-AGACTCGGGCCTACAATGGA-3' | 4 |
| Angio-poietin-1 (Angpt1) | F | 5'-ACGGGGGTCAATTCTAAG-3' | 5 |
| | R | 5'-GCCATTCCTGACTCCACA-3' | 6 |
| Vascular cell adhesion molecule-1 (Vcam1) | F | 5'-AAAAGCGGAGACAGGAGACA-3' | 7 |
| | R | 5'-AGCACGAGAAGCTCAGGAGA-3' | 8 |
| IL7 | F | 5'-ATTGAACCTGCAGACCAAGC-3' | 9 |
| | R | 5'-GCAACAGAACAAGGATCAGG-3' | 10 |
| Spp1 (osteo-pontin) | F | 5'-TGTGGAGTTTTAGAGATATTAGAT-AGTGGG-3' | 11 |
| | R | 5'-AACA CACTCTTAACACCACTAAA-TCACC-3' | 12 |
| GAPDH | F | 5'-TTGCTGTTGAAGTCGCAGGAG-3' | 13 |
| | R | 5'-TGTGTCCGTCGTGGATCTGA-3' | 14 |

1-4. Colony-Forming Cell (CFC) Assay

A colony-forming cell (CFC) assay was performed to measure the number of bone-marrow hematopoietic progenitor cells in blood from mice.

First, the mice were anesthetized, and 500 μl to 700 μl of blood was drawn from the hearts of the mice, and collected in a heparin tube. Thereafter, the collected blood was added to an ammonium chloride solution (Stem Cell Technologies, Inc. 1:10), and kept in ice for 15 minutes to remove red blood cells. The blood was shaken at intervals of 2 to 3 minutes to sufficiently remove the red blood cells, and centrifuged at 1,000 rpm for 7 minutes. A supernatant was removed, and washed with IMDM (Gibco) supplemented with 2% fetal bovine serum (FBS, Gibco). The washed cells ($3\times10^5$ cells per a mouse) were divided into three 35-mm dishes including a methylcellulose-based medium (Methocult, Stem cell) ($1\times10^5$ cells per a dish), and cultured for 2 weeks. Then, colonies formed on the flask were counted.

1-5. Flow Cytometry Analysis (FAC)

To determine whether there is a change in the number of the bone-marrow haematopoietic stem cells present in the bone marrows from the mice, NPY and PBS were injected to normal mice. After 60 minutes, the bone marrows were collected, and analyzed by flow cytometry analysis (FAC) using five antibodies Lineage, Sca-1, c-kit, CD48, and CD150, which were markers for the bone-marrow haematopoietic stem cells.

To analyze the bone-marrow haematopoietic stem cells, the bone marrows collected from the tibias and femurs of 4- to 6-week-old C57BL/6 mice was added in an ammonium chloride solution (Stem Cell Technologies, Inc. 1:4) to remove red blood cells. Thereafter, the red blood cells were washed with a PBS (Gibco) solution supplemented with 10% fetal bovine serum (FBS, Gibco) and 1% sodium azide (Sigma-Aldrich), and then centrifuged at 300×g for 10 minutes. Hemoblasts included in the bone marrow were removed with MAC beads (MiltenyiBiotec) using a biotinylated lineage antibody (MiltenyiBiotec), and the remaining cells were reacted with Sca-1-PECY7, c-kit-APC, CD150-PE, CD48-FITC (BD Science) antibodies at 4° C. for 30 minutes, and then analyzed using an LSRII (BD Science) flow cytometer.

1-6. Competitive Transplantation Assay

As an experimental method capable of determining the migration of bone-marrow haematopoietic stem cells and bone-marrow hematopoietic progenitor cells present in the bone marrows of the mice into blood, a competitive transplantation assay were performed.

A mixture of bone marrow cells ($2\times10^6$) of Ly5.2 (C57BL/6) donor mice and bone marrow cells ($2\times10^6$) of Ly5.1 (BoyJ) mice was injected to recipient mice whose whole bodies were exposed to 10 Gy irradiations (2×5 Gy) through the tail veins thereof. On the week 8 of transplantation of the bone marrow cells, blood was drawn from the recipient mice, and analyzed by an LSR II (BD science) flow cytometer using CD45.1-PE (BD Science), and CD45.2-FITC (BD Science) antibodies. Repopulating units (RU) are indicated using a calculation method represented by the following Equation 1.

$$\text{Repopulating unit (RU)} = (20 \times CD45.2\%)/(100 - CD45.2\%) \quad \text{[Equation 1]}$$

1-7. Micro-CT

The femurs were isolated from the mice, and refrigerated in 80% ethanol, and the bone density and the trabecular thickness were measured at a tissue thickness of 40 μm, an exposure time of 600 msec, a photon energy of 70 keV, and a current of 400 μA using a micro CT scanner (Inveon preclinical CT, Siemens Healthcare, Hoffman Estates, Ill.) for micro CT imaging. To measure a bone density (bone volume/total volume) and a trabecular thickness, volume fractions with 2.5×0.5×0.5 mm³ in the same portions of the femurs in each group were measured using Siemens Inveon software.

Example 2. Effect of Expressed Knockout Gene of Neuropeptide Y on Expression of Haematopoietic Stem Cell Adhesion Factors and Number of Haematopoietic Stem Cells in Blood To examine an effect on the expression of haematopoietic stem cell adhesion factors (Sdf-1a, Kit1, Angpt1, IL7, Vcam1, and Spp1) present in osteoblasts of mice whose a gene expressing neuropeptide Y is knock out (hereinafter referred to as an "NPY KO mouse"), and an effect on the number of the bone-marrow hematopoietic progenitor cells in blood, the following experiment was performed.

2-1. Determination of Expression Levels of Haematopoietic Stem Cell Adhesion Factors First, NPY KO mice and WT mice were purchased from Jackson Laboratory (Bar Harbor, Me., USA), and a bone marrow was taken from each mouse. A total of RNAs were extracted from the obtained bone marrow, and cDNA was then synthesized from the RNAs in the same manner as described in Example 1-3. Thereafter, the expression levels of Sdf-1a, Kit1, Angpt1, IL7, Vcam1, and Spp1, which were main adhesion factors involved in maintenance of the bone-marrow haematopoietic stem cells in the bone marrow, were analyzed.

The results are shown in FIG. 1.

As shown in FIG. 1, it could be seen that all the expression levels of the six factors more increased in the bone marrows of the NPY KO mice than the bone marrows of the WT mice ($p<0.05$, $n=3$ per group).

2-2. Measurement of Number of Bone-Marrow Hematopoietic Progenitor Cells in Blood To measure the number of the bone-marrow hematopoietic progenitor cells present in the blood from the NPY KO mice and the WT mice, an experiment was performed in the same manner as described in Example 1-4. Blood was drawn from the mice's hearts, and cell colonies were counted according to a CFC assay to examine the number of the bone-marrow hematopoietic progenitor cells present in the blood.

The results are shown in FIG. 2.

As shown in FIG. 2, it could be seen that the number of the bone-marrow hematopoietic progenitor cells in the blood from the NPY KO mice significantly decreased, compared to the WT mice ($p<0.05$, $n=3$ per group).

From these results, it was revealed that the number of the bone-marrow hematopoietic progenitor cells in the blood decreased since an increase in the expression levels of the bone-marrow haematopoietic stem cell adhesion factors present in the bone marrows of the NPY KO mice made it difficult to release the bone-marrow haematopoietic stem cells into the bloodstream.

Example 3. Effect of Neuropeptide Y of the Present Invention on Expression of Haematopoietic Stem Cell Adhesion Factors To examine an effect of neuropeptide Y on expression levels of adhesion factors involved in maintenance of the bone-marrow haematopoietic stem cells in the bone marrow, an experiment was performed in the same manner as described in Examples 1-2 and 1-3, as follows.

First, bone marrows were taken from 4- to 6-week-old C57BL/6 mice to collect bone-marrow mesenchymal stem cells (BM-MSCs). Thereafter, the BM-MSCs were cultured for 3 weeks in a medium for inducing the differentiation of osteocytes to differentiate into osteoblasts. On the 21$^{st}$ day, the BM-MSCs were treated with neuropeptide Y at a concentration of 0, 1, and 5 nM for 3 days, and osteocytes were recovered to examine the expression levels of the 6 adhesion factors using real-time quantitative PCR.

A schematic diagram for this experimental procedure is shown in FIG. 3, and the measurement results of the expression levels of the adhesion factors are shown in FIG. 4.

As shown in FIG. 4, it could be seen that the expression levels of Sdf-1a, Kit1, and Angpt1 in the osteocytes treated with neuropeptide Y decreased in a ration-dependent manner, compared to the osteoblasts (control) which were not treated with neuropeptide Y ($p<0.05$, $n=3$ per group).

From these results, it was revealed that the neuropeptide Y had a probability of inducing the release of the bone-marrow haematopoietic stem cells from the bone marrow into the blood by reducing the expression levels of the bone-marrow haematopoietic stem cell adhesion factors present in the osteoblasts.

Example 4. Effect of Neuropeptide Y of the Present Invention on Controlled Release of Bone-Marrow Haematopoietic Stem Cells in Bone Marrow into Blood 4-1. Determination of Expression Levels of Bone-Marrow Haematopoietic Stem Cell Adhesion Factors To examine an effect of neuropeptide Y according to one exemplary embodiment of the present invention on the expression levels of the bone-marrow haematopoietic stem cell adhesion factors in vivo, 50 µg/kg of neuropeptide Y was injected through the tail veins of the mice. After 60 minutes, bone marrows were taken from the tibias and femurs of the mice, and the expression levels of the adhesion factors were examined using a real-time quantitative PCR method.

The results are shown in FIG. 5.

As shown in FIG. 5, it was revealed that the expression levels of the main adhesion factors Sdf-1a, Kit1, Angpt1, and Vcam1 decreased ($p<0.05$, $n=3$ per group).

4-2. Measurement of Number of Bone-Marrow Hematopoietic Progenitor Cells in Blood (CFC Assay)

To determine whether the release of the bone-marrow hematopoietic progenitor cells into the blood due to a decrease in the expression levels of the adhesion factors was induced upon administration of neuropeptide Y according to one exemplary embodiment of the present invention, 50 µg/kg of NPY was injected through the tail veins of the mice, and blood was drawn from the mice's hearts at intervals of 15 minutes, 60 minutes, and 12 hours, and subjected to a CFC assay.

The results are shown in FIG. 6.

As shown in FIG. 6, it was revealed that the largest colony number of the bone-marrow hematopoietic progenitor cells was released into the blood after 60 minutes of injection of neuropeptide Y, and the colony number of the bone-marrow hematopoietic progenitor cells determined after 12 hours of injection of neuropeptide Y was similar to the colony number of the bone-marrow hematopoietic progenitor cells in the blood from the mice into which PBS was injected, indicating that the release of the bone-marrow hematopoietic progenitor cells by the neuropeptide Y was recovered to a normal state after 12 hours of the injection of neuropeptide Y ($p<0.05$, $n=3$ per group).

4-3. Measurement of Number of Bone-Marrow Haematopoietic Stem Cells in Blood (FAC Assay)

To examine an effect of the administration of neuropeptide Y according to one exemplary embodiment of the present invention on the number of the bone-marrow haematopoietic stem cells present in the bone marrow, the following experiment was performed according to the method as described in Example 1-5.

First, normal mice were divided into two groups (three mice in each group), and 50 μg/kg of neuropeptide Y and 100 μl of PBS (Gibco) were administered to the mice. After 60 minutes, bone marrows were taken from the mice. The bone-marrow haematopoietic stem cells obtained from the bone marrows were analyze by a FAC assay using five antibodies Lineage, Sca-1, c-kit, CD48, and CD150, which were markers for bone-marrow haematopoietic stem cells.

The results are shown in FIG. 7.

As shown in FIG. 7, it was revealed that the bone-marrow haematopoietic stem cells labeled with Lin−, Sca-1+, c-kit+, CD48−, and CD150+ decreased in the bone marrow when the neuropeptide Y was administered, compared to when PBS was administered ($p<0.05$, $n=3$ per group).

4-4. Determination of Release of Bone-Marrow Haematopoietic Stem Cells and Bone-Marrow Hematopoietic Progenitor Cells into Blood (Competitive Transplantation Assay)

To determine whether the bone-marrow haematopoietic stem cells and bone-marrow hematopoietic progenitor cells were released into the blood by administration of the neuropeptide Y according to one exemplary embodiment of the present invention, a competitive transplantation assay were performed according to the method as described in Example 1-6.

A mixture of bone marrow cells ($2\times10^6$) of Ly5.2 (C57BL/6) donor mice and bone marrow cells ($2\times10^6$) of Ly5.1 (BoyJ) mice was injected to recipient mice whose whole bodies were exposed to 10 Gy irradiations ($2\times5$ Gy) through the tail veins thereof. On the week 8 of transplantation of the bone marrow cells, blood was drawn from the recipient mice, and analyzed by an LSR II (BD science) flow cytometer using CD45.1-PE (BD Science), and CD45.2-FITC (BD Science) antibodies. Repopulating units (RU) are indicated using a calculation method represented by the following Equation 1.

$$\text{Repopulating unit (RU)} = (20 \times CD45.2\%)(100 - CD45.2\%) \quad \text{[Equation 1]}$$

The bone marrows (CD45.2+) of the mice into which the neuropeptide Y was injected, and the bone marrows (CD45.1+; for distinguishing from CD45.2+ cells) of the Ly5.1 mice were mixed together, and then injected into the normal (recipient) mice whose whole bodies were exposed to 10 Gy irradiations ($2\times5$ Gy). After 8 weeks of the injection, blood was drawn from the mice into which the a bone marrow mixture was injected, and the ratio of CD45.1+ and CD45.2+ cells was analyzed using a FAC assay.

The results are shown in FIG. 8.

As shown in FIG. 8, it was revealed that the ratio of the CD45.2+ cells in the bone marrows of the normal mice into which the neuropeptide Y was injected was reduced, compared to the CD45.2+ cells in the bone marrows of the mice into which PBS was injected as the control.

The RU values were lower in the mice into which PBS was injected than the mice into which the bone marrow mixture was injected ($p<0.05$, $n=3$ per group).

From these results, it was revealed that, since the bone-marrow haematopoietic stem cell that were the CD45.2+ cells were released into the blood in the case of the bone marrows of the mice into which the neuropeptide Y according to one exemplary embodiment of the present invention was injected, the number of the haematopoietic stem cells was lower than the bone-marrow haematopoietic stem cells that were the CD45.2+ cells present in the bone marrows of the mice into which PBS was injected, indicating that the donor-derived bone-marrow haematopoietic stem cells (donor-derived BM-HSCs) of the CD45.2+ cells were present at a small amount in the bone marrows of the recipient mice into which the bone marrow mixture was transplanted.

Example 5. Effect of Activities of Neuropeptide Y Receptor of the Present Invention on Expression of Bone-Marrow Haematopoietic Stem Cell Adhesion Factors in Bone Marrow and Release of Bone-Marrow Hematopoietic Progenitor Cells To determine whether the activities of the neuropeptide Y receptor are achieved through the expression levels of the bone-marrow haematopoietic stem cell adhesion factor by the neuropeptide Y and the Y1 receptor in the osteoblasts since the Y1 receptor that was a neuropeptide Y receptor was present in osteoblasts involved in the formation of bone in the bone marrow, the following experiment was performed.

5-1. Effect of Activation of Neuropeptide Y Receptor on Expression of Bone-Marrow Haematopoietic Stem Cell Adhesion Factors and Release of Bone-Marrow Hematopoietic Progenitor Cells into Blood As an experimental group, first, the mice into which 50 μg/kg of a Y1 agonist which acted similarly on the neuropeptide Y to react the Y1 receptor was injected through the tail veins thereof. As the control, the mice into which the neuropeptide Y and PBS was injected at an equivalent amount were used. After 60 minutes, the bone marrow was taken from each mouse, and the expression levels of the bone-marrow haematopoietic stem cell adhesion factors were examined using a real-time quantitative PCR method as described in Experimental Example 1-3.

Figure 9:
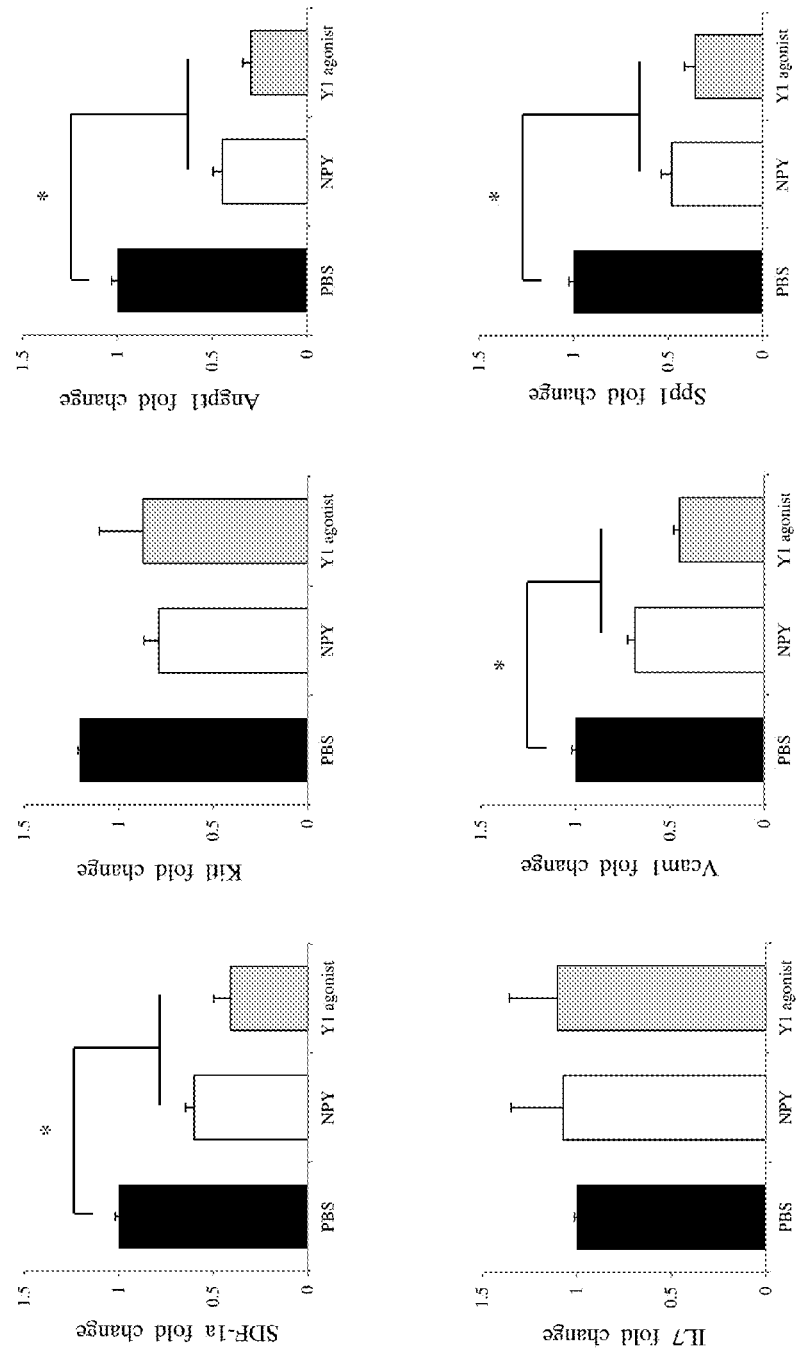
FIG. 9 is a diagram showing a change in the expression level of the bone-marrow haematopoietic stem cell adhesion factor upon administration of a neuropeptide Y receptor agonist (a Y1 agonist).

The results are shown in FIG. 9.

As shown in FIG. 9, it could be seen that the activation of the neuropeptide Y receptor generally further reduced the expression levels of Sdf-1a, Angpt1, Vcam1, and Spp1, which were the adhesion factors for bone-marrow haematopoietic stem cells, compared to when the neuropeptide Y was administered ($p<0.05$, $n=3$ per group).

To examine an effect of the activation of the neuropeptide Y receptor on the release of the bone marrow precursor cells into the blood, the colony number of the bone marrow precursor cells was also counted using a CFC assay as described in Example 1-4.

The results are shown in FIG. 10.

As shown in FIG. 10, it could be seen that the activation of the neuropeptide Y receptor increased the release of the bone-marrow hematopoietic progenitor cells into the blood, compared to when the neuropeptide Y was administered ($p<0.05$, $n=3$ per group).

5-2. Effect of Inhibition of Neuropeptide Y Receptor on Expression of Bone-Marrow Haematopoietic Stem Cell Adhesion Factors and Release of Bone-Marrow Hematopoietic Progenitor Cells into Blood This experiment was performed in the same manner as in Example 5-1, except that the mice into which 50 μg/kg of a Y1 antagonist which inhibited the neuropeptide Y from reacting with the Y1 receptor was injected through the tail veins thereof were used as the experimental group.

The results are shown in FIG. 11.

As shown in FIG. 11, it was revealed that the inhibition of the neuropeptide Y receptor did not reduce the expression levels of Sdf-1a, Kit1, Angpt1, and Vcam1, which were the adhesion factors for bone-marrow haematopoietic stem cells, but the administration of the neuropeptide Y generally reduced the expression of the bone-marrow haematopoietic stem cell adhesion factors (p<0.05, n=3 per group).

To examine an effect of the inhibition of the neuropeptide Y receptor on the release of the bone-marrow hematopoietic progenitor cells into the blood, an experiment was also performed in the same manner as in Example 5-1.

The results are shown in FIG. 12.

As shown in FIG. 12, it could be seen that the inhibition of the neuropeptide Y receptor reduced the release of the bone-marrow hematopoietic progenitor cells into the blood, compared to when the neuropeptide Y was administered (p<0.05, n=3 per group).

From these results, it could be seen that the migration of the bone-marrow hematopoietic progenitor cells into the blood was increased by the Y1 agonist, but was not increased by the Y1 antagonist, indicating that the release of the bone-marrow haematopoietic stem cells and bone-marrow hematopoietic progenitor cells into the blood by the neuropeptide Y occurred when the neuropeptide Y reacted with the Y1 receptor present in the osteoblasts to reduce the expression levels of the bone-marrow haematopoietic stem cell adhesion factors.

Example 6. Effect of Neuropeptide Y of the Present Invention on Prevention and Treatment of Osteoporosis To determine whether the release of the haematopoietic stem cells into the blood by administration of the neuropeptide Y according to one exemplary embodiment of the present invention was effective in preventing and treating osteoporosis, the following experiment was performed according to the methods as disclosed in Examples 1-1 and 1-7.

A schematic diagram for this experimental procedure is shown in FIG. 13.

First, three C57BL/6 female mice in each group, 12 weeks old, were subjected to an ovariotomy to establish an osteoporosis model. After a week, 50 µg/kg of neuropeptide Y and 100 µl of PBS (Gibco) were abdominally administered twice a day to the female mice at an interval of 12 hours for 3 weeks. As the control, the normal mice which were subjected to subcutaneous incision alone and into which 100 µl of PBS and 50 µg/kg of neuropeptide Y were abdominally administered were used. On the $22^{nd}$ day, the femurs of the mice were isolated, and refrigerated in 80% ethanol, and the bone density and the trabecular thickness were then measured using micro CT.

The results of the bone in the control and the osteoporosis model observed by micro-CT are shown in FIG. 14, the graphs plotted for the results of changes in the bone density and trabecular thickness of the mice are shown in FIG. 15.

As shown in FIG. 14, it was revealed that, when the neuropeptide Y was injected into the osteoporotic mice, the mice were observed to have a higher entire bone density in the imaged obtained by the micro-CT, compared to the osteoporotic mice into which PBS was injected. In the control model, it was also revealed that the mice into which the neuropeptide Y was injected were observed to have a higher entire bone density, compared to the mice into which PBS was injected.

Also, as shown in FIG. 15, it was revealed that the bone density (BV/TV, %) and trabecular thickness (mm) of the osteoporotic mice into which the neuropeptide Y was injected were higher than those of the osteoporotic mice into which PBS was injected, and the similar results were also observed in the control model (n=3 per group).

From these results, it could be seen that the release of the bone-marrow haematopoietic stem cells into the blood by the long-term administration of neuropeptide Y in the osteoporosis model inhibited a decrease in bone density and trabecular thickness of the osteoporotic mice by inducing the differentiation of the haematopoietic stem cells into the osteoclasts in the bone marrow, and a decrease in the number of the osteoclasts.

The invention claimed is:

1. A method of treating osteoporosis which comprises administering to a patient in need thereof a pharmaceutical composition comprising neuropeptide Y as an active ingredient.

2. The method according to claim 1, wherein the neuropeptide Y reduces the expression of cell adhesion factors in osteoblasts by acting on the neuropeptide Y receptor Y1 present in the cells.

3. The method according to claim 1, wherein the neuropeptide Y increases the release of bone marrow haematopoietic stem cells from the bone marrow into blood.

4. The method of claim 1, wherein the amount of neuropeptide Y administered is in a range of 0.01 to 1 mg/kg.

5. The method of claim 4, wherein the amount of neuropeptide Y administered is in a range of 0.05 to 0.1 mg/kg.

6. The method of claim 1, wherein the pharmaceutical composition further includes at least one pharmaceutically acceptable carrier.

7. The method of claim 6, wherein the pharmaceutically acceptable carrier is selected from one or more in the group consisting of saline, sterile water, a Ringer's solution, buffered saline, a dextrose solution, a maltodextrin solution, glycerol, and ethanol.

8. The method of claim 1, wherein the pharmaceutical composition further includes one or more auxiliary additives selected from the group consisting of an antioxidant, a buffer, and a bacteriostatic agent.

9. The method of claim 1, wherein the pharmaceutical composition is administered parenterally.

10. The method of claim 1, wherein the pharmaceutical composition is administered orally.

11. The method of claim 1, wherein the neuropeptide Y is administered once per day.

12. The method of claim 1, wherein the neuropeptide Y is administered in divided doses per day.

* * * * *